United States Patent [19]

Wayne

[11] Patent Number: 5,059,522
[45] Date of Patent: Oct. 22, 1991

[54] INTRINSIC ENZYME DOT BLOT IMMUNOASSAY OR INDENTIFICATION OF MICROORGANISMS

[76] Inventor: Lawrence G. Wayne, 3602 Myrtle St., Irvine, Calif. 92714

[21] Appl. No.: 234,415

[22] Filed: Aug. 18, 1988

[51] Int. Cl.$^5$ ................ G01N 33/543; G01N 33/548; G01N 33/569
[52] U.S. Cl. .................................... 435/7.2; 435/7.32; 435/7.4; 435/967; 435/970; 435/973; 435/975; 436/518; 436/530; 436/809
[58] Field of Search ................ 435/805, 810, 7.4, 973, 435/975, 7.32, 967, 970, 7.2; 436/518, 530, 809

[56] References Cited

U.S. PATENT DOCUMENTS

| | | | |
|---|---|---|---|
| 2,761,813 | 9/1956 | Goetz | 195/80 |
| 4,061,468 | 12/1977 | Lange et al. | 427/209 |
| 4,094,647 | 6/1978 | Deutsch et al. | 23/253 TP |
| 4,168,146 | 9/1979 | Grubb et al. | 422/56 |
| 4,200,690 | 4/1980 | Root et al. | 435/7 |
| 4,235,601 | 11/1980 | Deutsch et al. | 422/56 |
| 4,246,339 | 1/1981 | Cole et al. | 435/7 |
| 4,277,560 | 7/1981 | Gray et al. | 435/7 |
| 4,363,874 | 12/1982 | Greenquist | 435/7 |
| 4,366,241 | 12/1982 | Tom et al. | 435/7 |
| 4,376,110 | 3/1983 | Davis et al. | 436/513 |
| 4,391,904 | 5/1983 | Litman et al. | 435/7 |
| 4,407,943 | 10/1983 | Cole et al. | 435/7 |
| 4,442,204 | 4/1984 | Greenquist et al. | 435/7 |
| 4,447,529 | 5/1984 | Greenquist et al. | 435/7 |
| 4,461,829 | 7/1984 | Greenquist | 435/7 |
| 4,540,659 | 9/1985 | Litman et al. | 436/524 |
| 4,590,157 | 5/1986 | Chandler et al. | 435/7 |
| 4,591,570 | 5/1986 | Chang | 436/518 |
| 4,595,661 | 6/1986 | Cragle et al. | 436/534 |
| 4,642,285 | 2/1987 | Halbert et al | 435/7 |

FOREIGN PATENT DOCUMENTS

0051213 10/1981 European Pat. Off. .
2099578 12/1982 United Kingdom .

OTHER PUBLICATIONS

Immunoprecipitation Studies of Mycobacterial Catalase Wayne et al., Int. J. Sys. Bact; 26, 38, 1976.

Isolation and Characterization of Catalase Produced by Mycobacterium tuberculosis-Diaz et al, Am. Rev. Resp. Dis. 110, 312, 1974.

Reciprocal Immunological Distances of Catalase Derived from Strains of Mycobacterium avium, Mycobacterium tuberculosis, etc., Wayne et al., Int. J. Syst. Bact. 29, 19, 1979.

Serological, Taxonomic, and Kinetic Studies of the T and M Classes of Mycobacterial Catalase-Wayne and Diaz, Int. J. Syst. Bact., 32, 296, 1982.

(List continued on next page.)

Primary Examiner—David Saunders
Attorney, Agent, or Firm—Knobbe, Martens, Olson & Bear

[57] ABSTRACT

A method for performing an assay to differentiate between related taxa of micoorganisms, comprising the steps of providing a support having a plurality of zones, each zone comprising immobilized antibody to an enzyme found in a particular microorganism, wherein the antibody in the zone is specific to the enzyme, but not to corresponding enzyme of other taxa to be determined in the assay; contacting the zones with a sample suspected of containing one of the particular microorganisms; permitting enzyme in the sample to become bound by antibody in one or more of the zones; and determining which of the taxa were present in the sample by determining to which of the zones the enzyme has become bound. The determining step may comprise adding a substrate for the enzyme to the support after the enzyme has become bound thereto, wherein the substrate, after being acted on by the enzyme, creates a detectable signal. Also disclosed are an assay kit, an immunoreactive support, and a method for preparing the support, all for use in the method of the present invention.

7 Claims, 1 Drawing Sheet

OTHER PUBLICATIONS

Intrinsic Catalase Dot Blot Immunoassay for Identification of Mycobacterium tuberculosis, Mycobacterium avium, etc., Wayne et al, J. Clin. Micro 25, 1687, 1987.

Antigenic Differences Between Extracts of Actively Replicating and Synchronized Resting Cells of Mycobacterium tuberculosis, Wayne et al, Infect Immun. 24, 363, 1979.

Taxonomic Probability Matrix for use with Slowly Growing Mycobacteria–Wayne, et al., Int. J. Sys. Bact. 30, 528, 1980.

Identification of Mycobacteria by Specific Precipitation of Catalase with Absorbed Sera–Wayne and Diaz, J. Clin. Micro., 21, 721, 1985.

Immunoblotting and Dot Immunoblotting–Current Status and Outlook–Towbin and Gordon, Jour. Immunol. Meth. 72, 313, 1984.

Detection of a Novel Catalase in Extracts of Mycobacterium avium and Mycobacterium intracellulare–Wayne and Diaz, Infect. Immun., 56, 936, 1988.

Differentiation Between T-Catalases Derived from Mycobacterium avium and Mycobacterium, etc.–Wayne and Diaz, Int. J. Syst. Bact. 36, 363, 1986.

An Immunospecific Enzyme Assay for Horseradish Peroxidase–Ambler and Peters, Anal. Biochem., 137, 66, 1984.

A Dot-Immunobinding Assay for Monoclonal and Other Antibodies–Hawkes et al., Anal. Biochem., 119, 142, 1982.

Yolken et al, *Journ. Infect Dis.*, 142, 516–523, 1980.
Cocks et al., *Journ. Bact.* 110, 793–802, 1972.
Davidson et al., *J. Molec. Evolution*, 14, 251–258, 1979.
Gasser et al, *Journ. Bact* 106, 113–125, 1971.
Stanier et al, *Journ. Bact.* 102, 351–362, 1970.
Woulkalis et al, *Journ. Bact.*, 147, 36–45, 1981.
Hontebeyrie et al, *Int. Journ. Syst. Bact*, 25, 1–6, 1975.

INTRINSIC ENZYME DOT BLOT IMMUNOASSAY OR INDENTIFICATION OF MICROORGANISMS

BACKGROUND OF THE INVENTION

This invention relates to means for identifying microorganisms such as bacteria to a desired level of specificity by releasing selected enzymes from the microorganisms and exposing them to a panel of immobilized dots of specific antibody, and then determining which of the dots bind the enzyme.

The simplest and most definitive modern microbial identification techniques rely on some form of probe technology that is either nucleic acid or antibody based. Among the most frequently applied of the new commercially available technologies is the RNA-DNA hybridization probe system. See e.g., D. E. Kohne "Applications of DNA Probe Tests to the Diagnosis of Infectious Disease", *Amer. Prod. Rev.*, Nov. 20-29 (1986). With that system, a separate sample or probe must be processed for each of the species under consideration.

In recent years, solid-phase immunoassay techniques have been widely applied in basic research and clinical applications. To determine homogeneity or to identify unlabeled antigens, the classical methodologies of immunodiffusion and immunoelectrophoresis relying on precipitation have been available. More recently, as an extension of gel overlay techniques, the development methods for transferring proteins from the gel-phase of electrophoresis to a solid phase for immunoreaction permitted the optimal combination of high resolution of gel electrophoresis with the simplicity and sensitivity of solid-phase assays. One such methodology utilizes the transfer of proteins via direct application in the form of a dot. This type of methodology is frequently referred to as dot immunobinding, spot immunodetection or dot blot immunoassay. See e.g., H. Towbin and J. Gordon, "*Immunoblotting and Dot Immunobinding-Current Status and Outlook*" Journal of Immunological Methods 72:313-340 (1984).

In many antibody based immunodot procedures, a sandwich technique is usually required in which a standard primary ligand is applied to a membrane, which is then treated with the test sample. In order to visualize rapidly any binding that may occur, a third reagent, usually an antibody coupled to some standard enzyme, is applied next, and only then is a chromogenic substrate added that enables the visualization of the enzyme-antibody complex. See Towbin and Gordon, Id.

There is a need, however, for an accurate, rapid, and simple assay to differentiate or identify microorganisms. In particular, an assay kit that is simpler to construct, simpler to use, and less expensive would be highly desirable. The present invention is directed to such an assay.

SUMMARY OF THE INVENTION

The present invention exploits the observation that an optimal system using a microorganism's own enzymes for identifying members of a given genus would require that the desired enzyme retain its activity after reaction with antibody and that the desired enzyme be present in most or all members of the genus, but that antigenic regions (i.e., epitopes) occur on the enzyme molecule that are unique to the members of each species or taxon within that genus. The present invention provides a method for identifying microorganisms by a rapid, simple and accurate serological technique. It is based on the concept that an enzyme can be selected that is common to most or all of the taxa within some particular genus or other grouping of microorganisms of interest. The enzymes from the different taxa may all have similar chemical structure, but there will be some regions among the enzyme molecules that are unique to each taxonomic level, and these epitopes can be recognized with appropriate serologic probes.

In accordance with one aspect of the present invention, there is provided a method for utilizing antibody probes that are all directed at an enzyme produced by all of the microbial taxa under consideration, and binding of that enzyme is measured directly by addition of a chromogenic substrate, without intercession of an antibody-enzyme conjugate such as that required in the prior art. The idea of such an intrinsic-enzyme-based solid-phase immunoassay for purposes of microbial identification is especially attractive because it would eliminate the need for a second antibody, which is required for many solid-phase immunoassays, relying instead on the serologic binding of an indicator enzyme produced by the organism itself.

In one preferred embodiment, a number of different probes (each probe comprising one cross-absorbed antibody preparation that is specific for an enzyme of each of the possible taxa) are applied to different sites on a single membrane or other solid support, creating a multiple probe that can be treated as a single unit, at a substantial saving of material and labor costs. In the preferred embodiment, the membrane is porous in nature, and may be comprised, for example, of activated cellulose or nitrocellulose.

Thus, in accordance with one aspect of the present invention, there is provided a method for performing an assay to differentiate between related taxa of microorganisms, comprising the steps of providing a support having a plurality of zones, each zone comprising immobilized antibody to an enzyme found in a particular microorganism, wherein the antibody in the zone is specific to the enzyme, but not to corresponding enzyme of other taxa to be determined in the assay; contacting the zones with a sample suspected of containing one of the particular microorganisms; permitting enzyme in the sample to become bound by antibody in one or more of the zones; and determining which of the taxa were present in the sample by determining to which of the zones the enzyme has become bound. In one embodiment, the determining step comprises adding a substrate for the enzyme to the support after the enzyme has become bound thereto, wherein the substrate, after being acted on by the enzyme, creates a detectable signal.

In accordance with yet another embodiment of the invention, there is provided an assay kit for differentiating between related taxa of microorganisms, comprising a solid support; a plurality of zones, each zone comprising immobilized antibody to an enzyme found in a particular microorganism, wherein the antibody in the zone is specific to the enzyme, but not to corresponding enzyme of other taxa to be determined in the assay; and substrate for the enzymes to which the antibodies in the zones are specific, wherein the substrate, when acted on by enzyme bound by the antibody, creates a detectable signal. The kit may further comprise a control zone to which control antibody is immobilized, wherein the control antibody is specific to corresponding enzymes of all the taxa to be differentiated.

The present invention also includes an immunoreactive support for use in differentiating between related taxa of microorganisms, comprising a solid support; a plurality of zones of immobilized antibody on the support, each of which is specific to an enzyme of one of the taxa, but not to corresponding enzyme of other of the taxa, which enzyme is capable of acting on a substrate to produce a detectable signal. The support may further comprise a control zone having antibody immobilized thereto which binds the corresponding enzyme of all of the taxa.

Finally, the present invention includes a method for preparing a support for use in differentiating microorganisms, comprising the steps of providing a solid support, binding a plurality of different antibody spots thereto, each spot being specific to the corresponding enzyme of a different microorganism, wherein the enzyme from each of the microorganisms is capable of acting on a substrate to produce a detectable signal.

One advantage of the present invention over the prior art includes the fact that all probes in a set are on a single membrane, which eliminates the need for separate handling of many different probes in order to identify an organism. This results in a considerable saving in cost of materials by the user, as well as a significant saving in labor. In addition, the reduced number of manipulations produces a concomitant reduction in the chance of error in the procedure.

A further advantage of the present invention is the fact that the methodology can be adapted for use with many varieties of microorganisms, and it may be fine-tuned to numerous desired levels of specificity.

Another advantage of the present invention is that it can be read visually, with the "positive" reaction standing out from the common matrix background. In the prior art, it has frequently been necessary to obtain a quantitative reading in a given well, via use of an instrument, and that reading must subsequently be corrected with a background value read in an entirely different well.

A further advantage of the present invention over the prior art is that it has greater practical utility in the routine diagnostic laboratory than prior methodologies, which are more tedious to perform and are significantly more expensive. Further, previously used methodologies required quantitative assay and very high-titered antibody, because of the limited protein-binding capacity of the surface of polystyrene micro-wells, which are commonly used.

The intrinsic enzyme dot blot immunoassay described herein has several practical advantages over earlier methods. First, it utilizes an enzyme for identification purposes that is found in all taxa of cultivable microorganisms (with the occasional exception among some mutant strains). Second, the seroprecipitation assay and the enzyme-linked immunoassay ("ELISA") used in the prior art both depend on quantitative measurement of destruction of substrate by the enzyme-antibody complex and thus require precise standardization and volumetric measurement of reactants. The dot-blot method depends on the positive color reaction associated with the peroxidase function (or other detectable function) of the selected enzyme and is essentially qualitative; thus, it is more forgiving of minor quantitative variations in reagents. Third, the use of a small antibody dot in a larger membrane field reduces the uncertainties in interpretation of the contribution of nonspecific background reactions that are inherent in ELISAs; the clear zone around the dot is the control, and the contrast between dot and background is readily observed. Fourth, when using a porous membrane as a support, the porous structure permits immobilization of a much larger amount of immunoglobulin in a small zone than does the solid polystyrene surface of an ELISA well, eliminating a need for immunoaffinity purification of antibody. Finally, the use of multiple dots in a single membrane strip permits the test to be performed as a unit, instead of as a series of subtests as in seroprecipitation or ELISA.

DETAILED DESCRIPTION OF THE PREFERRED EMBODIMENT

The present invention provides a method for identifying bacteria or other microorganisms by a rapid, simple and accurate serological technique. It is based upon the concept that an enzyme can be selected that is common to most or all of the species or taxa within some particular genus or other grouping of microorganisms of interest. The enzymes from the different species may all have substantially similar chemical structure and function, but there will be some regions (epitopes) along the enzyme molecule that are unique to each species or other taxonomic level, and these epitopes can be recognized with appropriate serologic probes.

It should be emphasized that the present invention is applicable to virtually all microorganisms, such as bacteria, mycoplasma, protozoa, and the like. For example, in addition to mycobacteria, the invention may be applied to staphylococci, streptococci, and, indeed, all gram negative enteric pathogens. In fact, virtually all single-celled organisms are susceptible to identification by the present invention. While tests will usually be prepared to differentiate between related organisms, e.g., within the same genus, there is no reason that it cannot be used to differentiate between microorganisms of different genera. For example, where various unrelated microorganisms could cause the same symptoms in a patient, all could be included in the same test slide. In addition, tests could be prepared to give a comprehensive "snapshot" of all microorganisms present, for example, in the bowel of a patient.

The list of types of enzymes that can be used in the practice of the present invention is extensive, and those enzymes will be apparent to those of ordinary skill in the art. Although catalase is exemplified here as a preferred example, it should be noted that any of the peroxidases that can act on a colorimetric substrate can be used, and numerous examples of such enzymes are known and are presently used in colorimetric ELISA assays. In addition, dehydrogenases can be used in combination with a detectable substrate such as pyruvate, with the use of a tetrazolium salt as an indicator. Lactic dehydrogenase is one example of such an enzyme. Other enzymes that can be used include hydrolytic enzymes (hydrolases) and any enzyme that can form an insoluble detectable product from a soluble substrate. The insoluble product can be colored or radiolabeled. Finally, enzymes that act on relatively nonconductive substrates to form ions or other conductive products can be used to produce a detectable signal in the assay of the present invention.

Figure 1:
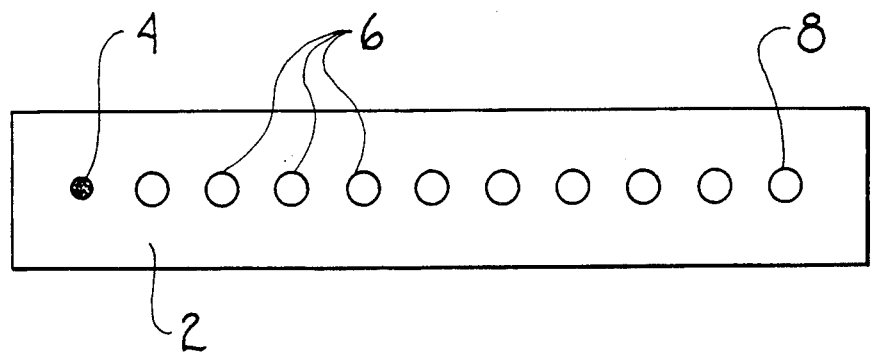
FIG. 1 is a plan view of a preferred embodiment of the present invention showing an unused or unreacted test strip or membrane.
Figure 2:
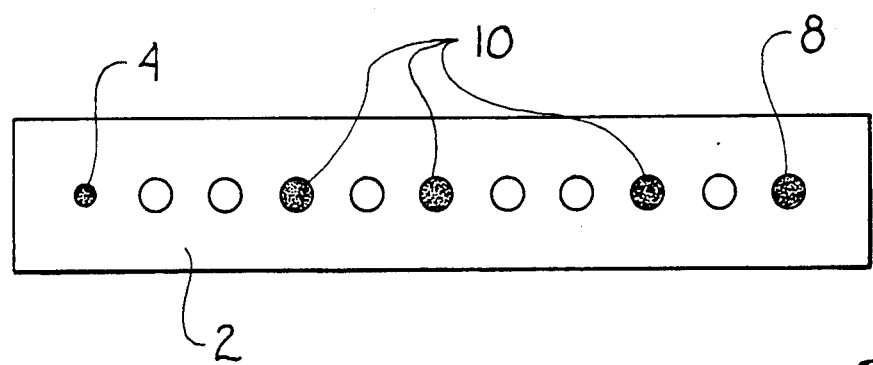
FIG. 2 is a plan view of a preferred embodiment of the present invention showing a used or reacted test strip or membrane.

The device of the present invention and its use may be readily explained by reference to FIGS. 1 and 2. FIG. 1 illustrates the unreacted or unused test strip 2, which is a solid support having a reference mark 4 and dots of cross-absorbed antibody 6, each dot 6 being specific to enzyme from a different microorganism for which the test is intended. The test strip 2 also includes a control spot or zone 8, which comprises antibody specific to enzyme of all of the microorganisms to which the test is directed.

To use the assay, sample suspected of containing microorganisms of interest is treated in such a way as to disrupt the microorganisms, and the test strip 2 is then dipped into the sample or a solution thereof. Thereafter, the strip 2 is contacted (as by dipping or other appropriate method) with a substrate solution. In the illustrated embodiment (FIG. 2), a colorimetric substrate is used. In FIG. 2, three of the dots 6 have enzyme bound thereto that reacts with the substrate, causing a color change in the positive dots 10. By referring to indicia on the strip 2 or other information supplied with the assay kit containing the strip 2, a user can determine which three microorganisms were present in the sample. Note that a color change in the control dot 8 indicates that the assay is good and that the enzyme in question is present in the sample.

A. Preparation of Antigen (Enzyme). One method for growing these cells, disrupting them, and separating the crude proteins has been described previously in L. Wayne and G. Diaz, "Immunoprecipitation Studies of Mycobacterial Catalase," *Int. J. Syst. Bacteriol* 26: 38–44 (1976), which is incorporated by reference herein. In summary, cells are grown in a nutrient medium in a manner such as that described in the referenced article, until optical density measurements indicate a cellular concentration, for example, of approximately $5 \times 10^7$ per ml. Subsequently, the cells may be agitated continuously on a rotary incubator-shaker at 37° C. and 120 rpm until the cellular concentration has increased approximately 10-fold, and are harvested as actively growing logarithmic phase cells.

Cells may also be cultured and processed without agitation. For example, supernatant culture medium from non-agitated cultures may be carefully aspirated to avoid disturbing the resting cells in the sediments. These sedimented cells may be suspended in, for example, load buffer [0.005M tris (hydroxymethyl) aminomethane-phosphate, pH 8.0] and harvested by centrifugation at $4,300 \times g$. On the other hand, the entire contents of the agitated culture flasks referred to supra may also be centrifuged at $4,300 \times g$. Thereafter, both types of cells may be treated in the same manner.

The centrifuged cells are typically separated from supernatant fluids, resuspended in fresh load buffer, and centrifuged again at $4,300 \times g$. The cells are then removed and suspended in fresh load buffer containing 0.1% Tween 80, transferred to calibrated centrifuge tubes, and centrifuged at $850 \times g$. The volume of packed cells should be noted, and the wash discarded. The cells may then be suspended in an equal volume of plain load buffer and disrupted by sonic treatment at 0° C. as described previously in L. Wayne and G. Diaz, "Isolation and Characterization of Catalase Produced by *Mycobacterium tuberculosis*,". *Am. Rev. Resp. Dis.* 110:312–319 (1974), which is incorporated herein by reference.

Sonic extracts may then be added to a suspension of diethylaminoethyl(DEAE)-cellulose (Sigma Chemical Co., St. Louis, Mo.), containing 250 mg of DEAE for each ml. of packed cells as measured before sonic treatment, in 100 ml of cold load buffer. After mixing, the DEAE with adsorbed cellular proteins is permitted to settle at 5° C. A cloudy, lipid-rich supernatant is discarded. The DEAE is washed and permitted to settle several times in fresh cold load buffer until the supernatant is only slightly opalescent. The DEAE is then resuspended in load buffer, transferred to a chromatographic column, and allowed to settle. The packed column is washed with load buffer until the effluent is clear; the washes are discarded. The bound protein is eluted with 0.5M NaCl buffer (equal portions of load buffer and one M NaCl in 0.05M phosphate, pH 6.5), using 30 ml of the buffer mixture per gram of DEAE. The eluate is sterilized by membrane filtration (Millipore Corp.).

These crude protein extracts may then be assayed by, for example, the method of Lowry et al. and dialyzed against appropriate buffers for immunoelectrophoresis and for immunization of rabbits. See, e.g., E. Layne, "Spectrophotometric and Turbidimetric Methods for Measuring Proteins," *Methods Enzymol.* 3:448 (1957).

An example of another method which may be utilized to prepare sufficient quantities of an antigen or enzyme has been set forth previously. See, e.g., L. Wayne and G. Diaz, "Serological, Taxonomic, and Kinetic Studies of the T and M Classes of Mycobacterial Catalase," *Int. J. Syst. Bacteriol.* 32: 296–304 (1982); and L. Wayne and G. Diaz, "Reciprocal Immunological Distances of Catalase Derived From Strains of *M. avium, M. tuberculosis*, and Closely Related Species," *Int. J. Syst. Bacteriol.* 29: 19–24 (1979). These articles are incorporated herein by reference.

B. Immunization and Preparation of Monoclonals and Polyclonals. Male New Zealand white rabbits were used, albeit other genera and species may be appropriate and useful. Immunization may be achieved, for example, by using Freund complete adjuvant in which the whole cells of the microorganism used are derived from the same cultures as were used to prepare a given cell sonic extract antigen. For example, a portion of washed packed bacilli was suspended in 10 volumes of distilled water and steamed for 20 minutes. After centrifugation, the supernatant was discarded and cells were resuspended in water and steamed again for 20 minutes. The cells were again separated by centrifugation and resuspended in water to yield a suspension corresponding to 15 mg/ml (dry weight). A 6-ml volume of the crude soluble protein antigen (1 mg of protein per ml of phosphate-buffered saline) was mixed with 6 ml of incomplete Freund adjuvant (Difco, Detroit, Mich.) at 0.4 ml of homologous whole cell adjuvant suspension and converted to a homogeneous paste by repeated flushing through a 20-gauge needle. The initial inoculum consisted of 1.0 ml into each of 4 subcutaneous sites and 0.1 ml into each of 2 intradermal sites. Animals were boosted after the first five weeks with 1 ml in each of two subcutaneous sites, and thereafter at 4–5 week intervals with 0.1 ml intravenously and 0.4 ml subcutaneously. Working samples of serum were derived from blood drawn one week after each boost.

C. Probe Preparation. After selection of the enzyme to be exploited for identification of the desired microorganisms, that enzyme is partially or completely purified from a strain of each of the species or other taxa for which a probe is required, by common protein fractionation procedures. A portion of each enzyme preparation is then used to immunize animals by standard procedures. The serum is tested for the desired antibodies to the enzyme batch that induced it, i.e., the homologous antigen. When antibody levels are high enough, each serum is cross-absorbed with excess amounts of enzyme preparation(s) from one or more of the species that was not used to induce that antibody, i.e., a heterologous species. The remaining free antibody globulin is separated from the resulting seroprecipitate and/or immune complex by ion exchange chromatography, or other suitable technology. The antibody is then tested to establish its potency against homologous enzyme/antigen, and to insure that it gives no significant cross-reaction with any of the heterologous enzymes. Alternatively, monoclonal antibodies may be produced from the enzyme from a strain of each of the taxa for which a probe is desired, and the optimal clones may be selected by testing against homologous and heterologous enzymes/antigen under the criteria applied to the cross-absorbed sera cited above. Methods for preparation of monoclonal antibodies against an identified antigen are well known. It may be necessary to use pools of monoclonal antibodies to assure that the working preparation has antibody against to all members of that taxon.

D. Preparation of the Probe Matrix. Small dots of a suitable dilution of each of the cross-absorbed globulin preparations or monoclonal antibody pools is supplied in a fixed pattern to different sites of a desired support, such as a porous plastic membrane or a similar surface, and the antibody is allowed to attach firmly by adsorptive forces, hydrophobic interaction, ligand coupling or covalent coupling. If desired, any of the well known immobilization techniques may be used to directly or indirectly bind the antibody to the support. Agents such as protein, detergent, and/or other suitable materials are then applied to block adsorptive or other binding sites on the membrane that are not occupied by an antibody dot. After brief rinsing, the membrane is ready for immediate use; alternatively, it may be dried and stored for later use.

E. The Test. An extract of the organism to be identified is made by sonic or chemical disruption, autolysis, or simple solvent treatment, depending upon the fragility of the test group of organisms and the stability of the test enzyme. The probe matrix, that is, the membrane with antibody dots, is soaked in the extract, rinsed to remove unbound enzyme, and placed in a solution of substrate. The selected substrate or substrate mixture is responsive to the enzyme of interest and produces a colored, fluorescent, conductive, or other detectable reaction product under the influence of the enzyme that remained at the site of the corresponding antibody probe dot. The appearance of a colored dot or other detectable reaction product at a site on the membrane indicates that the unique antibody at that site has recognized and bound the enzymes; i.e., the unknown organism belongs to the taxon that produced the enzyme that was used to induce that antibody, and not to taxa corresponding to the antibody probes at other sites on the membrane. By utilizing dots containing mixtures of antibodies, for example, the test can be further fine-tuned to different desired levels of specificity.

EXAMPLE 1

This methodology has been tested successfully using the enzyme catalase from selected members of the clinically important genus Mycobacterium. See, e.g., L. G. Wayne and G. A. Diaz, "Intrinsic Catalase Dot Blot Immunoassay For Identification of *Mycobacterium tuberculosis, Mycobacterium avium*, and *Mycobacterium intracellulare*," *Journal of Clinical Microbiology* 25; 1687-1690 (1987), which is incorporated herein by reference. However, the principle is essentially universal in application to different groups of microorganisms, with different selected enzymes. Strains utilized include *M. avium, M. intracellulare, M. tuberculosis* and *M. xenopi.*

As noted previously, an optimal system for identifying members of a given genus would require that the desired enzyme retain its activity after reaction with antibody and that the desired enzyme be present in most members of the genus, but that epitopes occur on the enzyme molecule that are unique to the members of each species or taxon within that genus. In the genus *Mycobacterium*, the catalase enzyme meets these criteria. Two classes of catalase have been recognized among the mycobacteria; one of the classes is known as T-catalase. Large batches of partially purified T-catalase required for immunization of rabbits and cross-absorbtion of antibody were prepared from *M. tuberculosis* H37 RV, *M. avium* SJB-2 and *M. intracellulare* Boone by methods described in L. G. Wayne and G. A. Diaz, "Serological, Taxonomic and Kinetic Studies of the T & M Classes of Mycobacteria Catalase", *Int. J. P. Syst. Bacteriol.* 32; 296-304 (1982), which is incorporated herein by reference. They were confirmed to be free of M-Catalase by the zero-order kinetic assay in the presence of 3-amino-1,2,4-triazole.

For preparing the smaller samples of crude catalase needed for serologic testing, the test strains were grown in single tubes containing 10 ml of a medium prepared from Dubos Broth Base (Difco) enriched with Dubos Oleic Albumin complex (Difco) and 1% (wt/vol) glycerol. The cells were harvested, washed, and sonicated in the original screw-capped culture tube, using the cup-horn adapter to a model 185D sonifier (Heat Systems-Ultrasonics, Inc.) as described in L. G. Wayne and G. A. Diaz, "Identification of Mycobacteria by Specific Precipitation of Catalase With Absorbed Sera," *J. Clin. Microbiol.* 21: 721-725 (1985). The activity of the extracts was then determined by assaying for T-catalase in the presence of aminotriazole.

New Zealand rabbits were immunized with partially purified T-catalase isolated from *M. avium* SJB-2, *M. intracellulare* boone, and *M. tuberculosis* $H_{37}RV$, and the sera retitrated against homologous antigen by the seroprecipitation supernatant assay as described previously (Wayne and Diaz, 1982). The sera were treated with 50% saturated ammonium sulfate to precipitate the immunoglobulins which were recovered by centrifugation and dissolved in a small volume of 0.01M phosphate-buffered saline (pH 7.5) preserved with 0.1 mg of thimerosal per ml ("PBSM"); residual ammonium sulfate was removed by passage over Sephadex G-25 (Pharmacia) equilibrated with PBSM. Based on the homologous antigen titers of the globulin preparations and previously reported immunologic distances of T-catalase from heterologous species, a portion of each globulin solution was cross-absorbed with a twofold excess of PBSM solution of T-catalase from a species with the lowest immunologic distance score to the homologous catalase (i.e., antibodies to T-catalase from *M. tuberculosis* $H_{37}RV$, *M. avium* SJB-2, and *M. intracellulare* Boone were cross-absorbed by T-catalase from M. avium SJB-2, M. intracellulare Boone, and M. avium SJB-2, respectively). After overnight incubation, the preparations were centrifuged, and excess, unprecipitated catalase was removed from supernatant fluids by absorption onto DEAE-Sephacel (Pharmacia) as described previously (Wayne and Diaz, 1985).

The desired dilutions of cross-absorbed and unabsorbed immunoglobulin were made in PBSM.

Samples of one microliter were spotted to nitrocellulose membranes (BioRad) and allowed to dry at room temperature. The sheets were soaked in 0.05M bicarbonate buffer (pH 9.4) for 18 hours at 5° C. An equal volume solution of two mg of bovine albumin fraction V per ml in 0.1M phosphate buffer (pH 7.5), preserved with 0.1 mg of thimerosal per ml, was then added to the bicarbonate buffer and allowed to block the membrane at 37° C. for 60 minutes. The blocking fluid was aspirated, the membrane was washed once with PBSM, and strips of membrane containing the desired immunoglobulin dots were cut and transferred to individual test tubes for reaction with selected catalase solutions.

In a typical assay, a nitrocellulose strip (6 by 45 mm), bearing four immunoglobulin spots and a pencil mark for orientation was soaked for two hours at 37° C. in two ml of PBSM containing the T-catalase to be tested in a screw-capped tube (13 by 100 mm) lying flat. After incubation and aspiration of unreacted catalase, the strips were washed twice with PBSM. The membrane was then transferred to a clean tube and flooded with 2 ml of freshly prepared solution containing 500 micrograms of 3, 3'-diaminobenzidine (Sigma) and 30 micrograms of $H_2O_2$ per ml of 0.01M phosphate buffer in saline (pH 7.2). After 30 minutes of incubation at room temperature, the diaminobenzidine solution was aspirated and the strip was soaked in $H_2O$ for 10 minutes and placed on blotting paper to dry. The appearance of a brown spot at the site of a globulin dot indicated specific binding of the T-catalase.

EXAMPLE 2

Each of the test immunoglobulin products of Example 1 was evaluated before and after cross-absorbtion by spotting one-microliter dots of a twofold dilution series corresponding to a range of undiluted through 1:32 dilution equivalents of the original sera from which the globulins were derived. Each product was tested against homologous antigen and the heterologous T-catalase used to cross-absorb it. Cross-absorption diminished the homologous reaction to varying degrees, depending upon the immunologic relatedness of the catalase, and effectively eliminated the heterologous reactions.

A survey of crude mycobacterial sonic extracts was performed, using nitrocellulose strips primed with a 1-microliter (monitor) dot and 1-microliter dots of indicated dilutions of cross-absorbed immunoglobulin G to T-catalase from M. tuberculosis $H_{37}RV$ (10), M. Avium SJB 2 (1:16), and M. intracellulare TMC 1403 (1:4). The monitor dot was made with a mixture of unabsorbed immunoglobulin against T-catalase from M. tuberculosis (1:32), M. avium (1:16), and M. kansasii (TMC 1201) (1:32) and was used as a positive, nonspecific control to confirm the presence of an adequate amount of mycobacterial T-catalase. A positive reaction was demonstrated by the appearance of a discrete solid brown dot at the site of a reference globulin, which persisted after the test strip had completely dried. After a preliminary series had been run, it became evident that a challenge load of at least 0.3 U of T-catalase was required for a test strip to yield consistent results. This amount is usually available in the sonic extract of a 10-ml liquid culture that had reached an $A_{580}$ in excess of 0.50 at harvest.

The results of testing extracts of 93 strains, representing 11 species or complexes of slow growing mycobacteria, are recorded in Table 1.

TABLE 1

Responses of extracts of strains of mycobacterial species in dot-blot immunoassay on cross-absorbed antibody to selected T-catalases

| Extract | M. tuberculosis | M. avium | M. intracellulare | MONITOR ONLY |
|---|---|---|---|---|
| M. avium | 0 | 16 | 0 | 0 |
| M. bovis | 5 | 0 | 0 | 0 |
| M. gastri | 0 | 0 | 0 | 0 |
| M. intracellulare | 0 | 0 | 19 | 2 |
| M. kansasii | 0 | 0 | 0 | 17 |
| M. malmoense | 0 | 0 | 0 | 2 |
| M. scrofulaceum | 0 | 0 | 0 | 6 |
| M. simiae | 0 | 0 | 0 | 3 |
| M. szulgai | 0 | 0 | 0 | 3 |
| M. tuberculosis | 15 | 0 | 0 | 0 |
| M. xenopi | 0 | 0 | 0 | 4 |

Of 5 strains of M. bovis and 15 of M. tuberculosis, all reacted with the monitor dot and with the anti-M. tuberculosis dot, but with no other immunoglobulin. 16 strains corresponding to serovars that represent M. avium were tested; all gave a positive monitor reaction and reacted with the anti-M. avium immunoglobulin dot. 21 strains that corresponded to serovars that represented M. intracellulare gave positive monitor reactions, but only 19 reacted with the anti-M. intracellulare dot. One of the samples that failed to react was derived from a serovar 7 strain (P-49), and the other was from a serovar 18 (Melnick); both strains produced more M-catalase than T-catalase and were urease positive. The M-catalase from both failed to react with specific antibody to M-catalase from M. scrofulaceum, M. simiae, M. gordonae, M. szulgai, or M. asiaticum by the seroprecipitation method described previously (Wayne and Diaz, 1982).

Extracts of 36 strains, representing Mycobacterium gastri, M. kansasii, M. malmoense, M. scrofulaceum, M. simiae, M. szulgai, and M. xenopi exhibited positive reactions for T-catalase on the monitor dot, but not on any of the three species-specific dots. Extracts of 4 strains of M. gordonae, two of M. terrae, two of M. nonchromogenicum, and three of M. triviale failed to react with the T-catalase monitor dot and are not included in Table 1. The later three species comprised the "terrae" complex and have previously been reported to produce only M-catalase (Wayne and Diaz, 1982). While M. gordonae does produce traces of T-catalase, M-catalase is present in great excess and extracts prepared as described for this test did not yield sufficient T-catalase to provide a satisfactory control dot response.

The data in Table 1 represent exposure of three species-specific antibody dots to each of 93 mycobacterial extracts. Of the 57 antibody dots exposed to an extract of homologous species, 55 gave positive reactions, for a sensitivity of 96.5%. This figure may be too conservative since the two strains (P-49 and Melnick) representing serovars 7 and 18, respectively, which are nominally *M. intracellulare* serovars but which failed to react with the corresponding anti-T-catalase dot, gave reactions in tests for urea and M-catalase that would be sufficient to cause their rejection in a phenetic taxonomic probability matrix. See, e.g., L. G. Wayne et al., "Taxonomic Probability Matrix for Use With Slowly Growing Mycobacteria", *Int. J. P. Syst. Bacteriol.* 30: 528–538 (1980). Serovars can cross species lines; an example is the demonstration of serovar 18 reactivity in many strains of *M. simiae*. In the present case, neither of the M-catalases from the two peculiar strains reacted with antibody to M-catalase from *M. simiae* or 4 other species, so their identities remain unresolved.

Of the 222 antibody dots exposed to extracts of heterologous species, none gave a positive reaction, for a specificity score greater than 99.5%. It must be pointed out that the reaction of T-catalase from nominal *M. bovis* with the antibody to T-catalase from *M. tuberculosis* is consistent with current recognition of the synonymy of these two species, as reflected in a high order of DNA-DNA homology between them.

The three species represented in the test as evaluated here account for over 86% of the pathogenic or potentially pathogenic mycobacteria reported by state laboratories. *M. kansasii*, *M. scrofulaceum*, and members of the *M. fortuitum* complex in the aggregate account for another 12.3% of the opportunistic pathogens, and the remaining 1% are distributed among at least 6 other species. Most of these species have been shown to produce T-catalase that exhibit some degree of evolutionary divergence from one another, so it seems likely that a dot-blot system can be developed that might permit identification of almost all clinically significant cultivable mycobacteria.

What is claimed is:

1. A method for performing an assay to determine the presence of one or more related taxa of microorganisms, comprising the steps of:
   providing a support having a plurality of first zones, each said first zone comprising immobilized antibody to an enzyme found in a different taxon of microorganism, wherein each antibody in each of said first zones is specific to said enzyme of one taxon, but not to a corresponding enzyme of other related taxa to be determined in said assay, and a control zone having antibody immobilized thereto which binds said corresponding enzyme of all said related taxa;
   contacting said zones with a sample suspected of containing one of said microorganisms or an extract thereof;
   permitting enzyme in said sample to become bound by antibody in one or more of said zones; and
   determining which of said taxa were present in said sample by determining to which of said zones said enzyme has become bound.

2. The method of claim 1, wherein said determining step comprises:
   adding a substrate for said enzyme to said support after said enzyme has become bound thereto, wherein said substrate, after being acted on by said enzyme, creates a detectable signal; and
   detecting said signal.

3. An assay kit for differentiating between related taxa of microorganisms, comprising:
   a solid support;
   a plurality of first zones on said support, each said first zone comprising immobilized antibody to an enzyme found in a different taxon of microorganism, wherein each antibody in each of said first zones is specific to said enzyme of one taxon, but not to a corresponding enzyme of other related taxa to be determined in said assay, and a control zone to which control antibody is immobilized, wherein said control antibody is specific to said corresponding enzyme of all said taxa to be differentiated; and
   substrate for said enzyme to which said antibodies in said zones are specific, wherein said substrate, when acted on by enzyme bound by said antibodies, creates a detectable signal.

4. The kit of claim 3, wherein said support has at least three first zones.

5. An immunoreactive support for use in differentiating between related taxa of microorganisms, comprising:
   a solid support;
   a plurality of first zones of immobilized antibody on said support, each of which is specific to an enzyme of one of said taxa, but not to a corresponding enzyme of other of said related taxa, which enzyme is capable of acting on a substrate to produce a detectable signal; and
   a control zone having antibody immobilized thereto which binds said corresponding enzyme of all of said taxa to which antibody in said first zones on said support is specific.

6. The support of claim 5, wherein said support has at least three first zones.

7. A method for preparing a support for use in differentiating microorganisms, comprising the steps of:
   providing a solid support;
   binding a plurality of different first antibody spots thereto, each said first spot being specific to the same enzyme of a different taxon of microorganism, but not to a corresponding enzyme of other related taxa, said enzyme being capable of acting on a substrate to produce a detectable signal; and
   binding a control antibody spot thereto, which control spot binds said corresponding enzyme of all of said taxa to which antibody in said first spots on said support is specific.

* * * * *